United States Patent [19]

Schoendorfer et al.

[11] Patent Number: 5,076,273
[45] Date of Patent: Dec. 31, 1991

[54] METHOD AND APPARATUS FOR DETERMINATION OF CHEMICAL SPECIES IN BODY FLUID

[75] Inventors: Donald W. Schoendorfer; William R. Miller, both of Santa Ana, Calif.

[73] Assignee: Sudor Partners, Santa Ana, Calif.

[21] Appl. No.: 611,460

[22] Filed: Nov. 13, 1990

Related U.S. Application Data

[63] Continuation of Ser. No. 510,471, Apr. 18, 1990, abandoned, which is a continuation of Ser. No. 241,707, Sep. 8, 1988, Pat. No. 4,957,108.

[51] Int. Cl.⁵ ............................................... A61B 5/00
[52] U.S. Cl. ............................ 128/632; 128/636; 128/760; 128/771
[58] Field of Search ............... 128/632, 636, 637, 760, 128/771; 604/312, 328; 422/58

[56] References Cited

U.S. PATENT DOCUMENTS

| | | | |
|---|---|---|---|
| 3,552,929 | 1/1971 | Fields | 23/253 |
| 4,190,060 | 2/1980 | Greenleaf | 128/760 |
| 4,287,153 | 9/1981 | Towsend | 422/56 |
| 4,329,999 | 5/1982 | Phillips | 128/760 |
| 4,341,207 | 7/1982 | Steer et al. | 128/155 |
| 4,360,015 | 11/1982 | Mayer | 128/156 |
| 4,444,193 | 4/1984 | Fost et al. | 128/632 |
| 4,542,751 | 9/1985 | Webster et al. | 128/760 |
| 4,595,011 | 6/1986 | Phillips | 128/636 |
| 4,631,174 | 12/1986 | Kondo | 422/56 |
| 4,667,665 | 5/1987 | Blanco et al. | 604/378 X |
| 4,706,676 | 11/1987 | Peck | 128/632 |
| 4,732,153 | 3/1988 | Phillips | 128/636 |
| 4,756,314 | 7/1988 | Eckenhoff et al. | 128/760 |
| 4,821,733 | 4/1989 | Peck | 128/636 |
| 4,957,108 | 9/1990 | Schoendorfer et al. | 128/632 |

FOREIGN PATENT DOCUMENTS

WO89/04630 6/1989 PCT Int'l Appl. .

*Primary Examiner*—Lee S. Cohen
*Attorney, Agent, or Firm*—Knobbe Martens Olson & Bear

[57] ABSTRACT

Disclosed is a method and apparatus for the non-invasive determination of one or more preselected analytes in a body fluid expressed through the skin. The fluid is collected in a dermal concentration patch and concentrated by driving off a portion of the substantial water fraction under the influence of body heat. The analyte is optimally complexed with an immobilized specific binding partner and an indicium of the presence of the analyte is visually expressed.

30 Claims, 1 Drawing Sheet

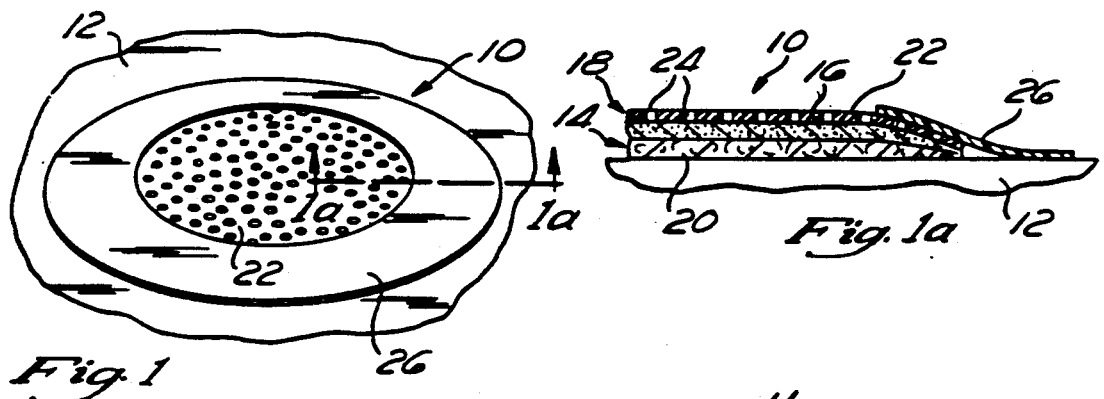
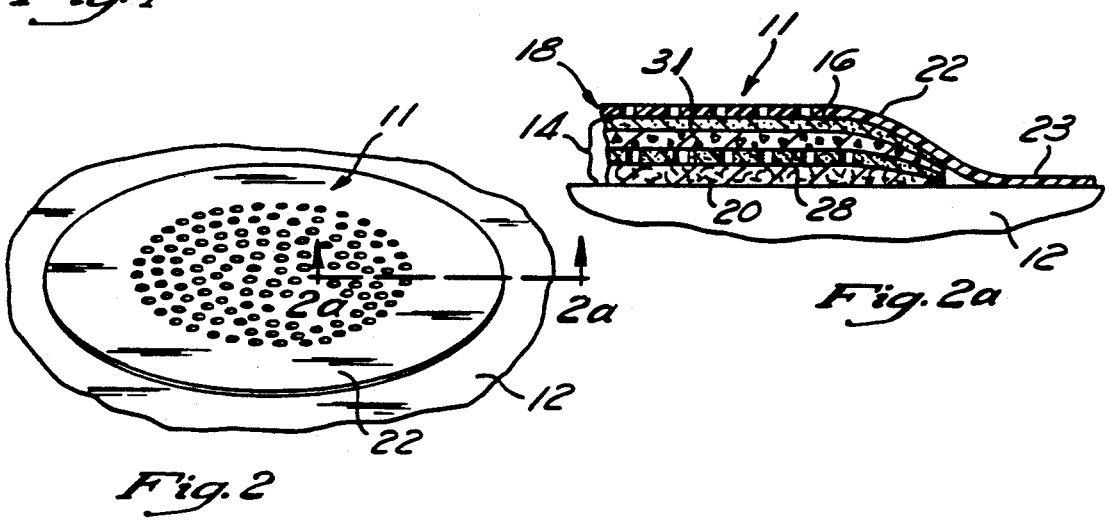
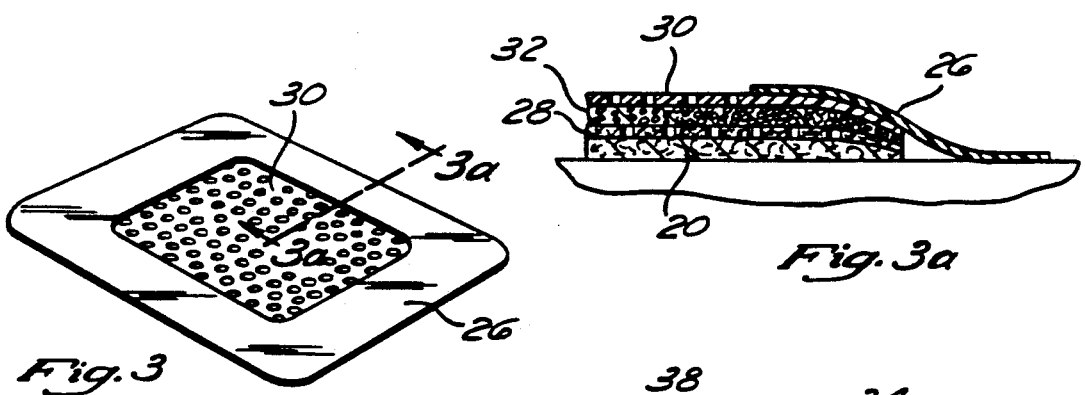

METHOD AND APPARATUS FOR DETERMINATION OF CHEMICAL SPECIES IN BODY FLUID

This application is a continuation of application Ser. No. 510,471, filed 4/18/90 now abandoned, is a continuation of application Ser. No. 241,707, filed 9/8/88, now U.S. Pat. No. 14,957.

BACKGROUND OF THE INVENTION

The present invention relates to diagnostic kits for determining the presence of one or more analytes in a fluid sample. More particularly, the present invention relates to a dermal concentration patch for increasing the concentration of an analyte expressed through the skin to a conveniently measurable level.

The determination of a patient's physiological status is frequently assisted by chemical analysis for the existence and/or concentration of predetermined chemical species in a body fluid. These tests, which are typically conducted in the physician's office or in the hospital, may be characterized by their collection technique as invasive, such as analyses of blood, or non-invasive, such as analyses of urine and perspiration.

Blood is frequently analyzed for a wide variety of components, and clinical laboratories are generally equipped with instrumentation which can provide a highly quantitative profile of the blood's composition. However, blood collection is inherently invasive, and therefore attended by several disadvantages. Analyses based upon collection of a sample of blood are generally restricted to the physician's office or clinical laboratory, which reduces convenience for ambulatory patients and greatly increases cost. In addition, some risks associated with an invasive procedure can range from undesirable at best to unacceptable, depending upon the condition of the patient, and the nature and necessity of the test desired to be performed.

Many analytes or metabolites of interest can additionally be detected in urine, which is characterized by its predictable supply and non-invasive collection. However, as will become apparent, urine analysis is not well suited for use in the principal intended application of the concentration patch of the present invention.

Perspiration is, under certain circumstances, an ideal body fluid for analysis in the determination of physiological status. Its non-invasive collection renders it suitable for use out of the physician's office, and its similarity to blood in terms of its content of biological molecules renders it suitable for a wide range of physiological testing.

Thus, a variety of diagnostic kits for monitoring an analyte in sweat have been developed. For example, U.S. Pat. No. 3,552,929 to Fields, et al. discloses a bandaid-type test patch particularly suited for determining the chloride ion concentration in perspiration as a method of diagnosing cystic fibrosis. The apparatus disclosed in Fields comprises an absorptive sweat collecting pad with an impermeable overlying layer for the purpose of preventing evaporation. When the absorptive pad is saturated, the patch is removed from the skin and exposed to a series of strips impregnated with incremental quantities of silver chromate or silver nitrate, the color of which undergoes a well known change upon conversion to the chloride salt.

U.S. Pat. No. 4,706,676 to Peck discloses a dermal collection device which comprises a binder to prevent reverse migration of an analyte, a liquid transfer medium which permits transfer of an analyte from the dermal surface to the binder, and an occlusive cover across the top of the liquid transfer medium and binder.

Peck discloses application of the dermal collection patch in the detection of human exposure to various environmental chemicals. After the dermal collection device has been worn on a patient's skin for a period of time, the patch is removed for analysis. Analysis requires chemically separating the bound substance of interest from the binding reservoir and thereafter undertaking qualitative and/or quantitative measurement by conventional laboratory techniques.

The prior art generally suffers from one or more important limitations when convenient field use of a diagnostic test patch is desired. In particular, prior art diagnostic test patches are generally only useful for determining the presence of analytes such as halide ions, which are present in sweat in relatively high concentrations. Other prior art dermal patches are merely collection devices from which the analytes must later be separated and concentrated or otherwise prepared for analysis in accordance with known laboratory techniques. In addition, the occlusive outer layer type devices of the prior art are susceptible to the problem of back diffusion of perspiration and/or analytes contained therein.

Thus, there remains a need in many diverse applications for a method and apparatus for the noninvasive determination of a preselected analyte in a body fluid such as perspiration, which can be utilized to detect the presence of low-concentration analytes in perspiration without the need for conventional instrumentation. The test kit should be low-cost and suitable for convenient use by non-medical personnel.

SUMMARY OF THE INVENTION

In overcoming the foregoing limitations of the prior art, there has been provided in accordance with one aspect of the present invention a dermal concentration patch for concentrating components of a body fluid under the influence of body heat, which comprises a concentration zone in communication with a source of body fluid and a discharge zone which is exposed to the atmosphere to permit escape of at least a portion of the substantial water component and other undesired components in the body fluid. In one preferred embodiment, the dermal concentration patch is provided with a selective volatile retention layer for use in monitoring the presence of a selected volatile component. Where the volatile is ethanol, for example, the volatile retention layer may comprise calcium sulfate crystals or other materials known in the art for their ability to capture the desired volatile.

In one embodiment, a hydrophobic membrane is provided to separate the concentration zone from the discharge zone, by preventing the passage of the fluid phase but permitting the escape of the vapor phase of the volatile components. The transition of body fluid accumulated in the concentration zone to the vapor phase is accelerated under the influence of body heat, thereby concentrating the non-volatile and less volatile components in the concentration zone. Alternatively, the concentration zone and the discharge zone may be separated by a hydrophilic layer, which would permit passage of the fluid phase into the discharge zone.

In a preferred embodiment of the present invention, the concentration patch further comprises an immobilized specific binding partner for an analyte to be determined in the body fluid. The specific binding partner may be immobilized to either a porous support such as cotton gauze, or to a plurality of microbeads disposed in the concentration zone. Alternatively, the specific binding partner can be immobilized to the filter separating the concentration and discharge zones.

In accordance with a further embodiment of the present invention, there is provided a method for determining the presence of an analyte in a body fluid, comprising the steps of first accumulating a quantity of a body fluid from a subject mammal, thereafter removing water vapor from the fluid under the influence of body heat to concentrate the non-volatile analytes contained in the fluid, and binding at least one concentrated analyte in the fluid to an immobilized specific binding partner of that analyte. The concentration of the bound analyte is thereafter expressed through any of a variety of immunoassay techniques well known in the art, such as an enzyme-linked immunoassay to reveal a color change in response to the presence of bound analyte.

Further features and advantages of the present invention will become apparent from the Detailed Description of Preferred Embodiments which follows, taken together with the claims and appended figures hereto.

BRIEF DESCRIPTION OF THE DRAWINGS

FIG. 1 is a perspective view of a dermal concentration patch according to one embodiment of the present invention.

FIG. 1a is a cross-sectional view along the line 1a—1a of the dermal concentration patch of FIG. 1.

FIG. 2 is a perspective view of a dermal concentration patch according to a second embodiment of the present invention.

FIG. 2a is a cross-sectional view along the line 2a—2a of the dermal concentration patch of FIG. 2.

FIG. 3 is a perspective view of a third embodiment of the dermal concentration patch of the present invention.

FIG. 3a is a cross-sectional view along the line 3a—3a of the patch of FIG. 3.

FIG. 4 is a perspective view of one embodiment of a reagent packet for use in effecting a color change responsive to the presence of analyte in the concentration patch of the present invention.

FIG. 5 is an exploded elevational schematic view of a fourth embodiment of the present invention.

DETAILED DESCRIPTION OF PREFERRED EMBODIMENTS

Referring to FIG. 1, there is disclosed a dermal concentration patch 10 according to one embodiment of the present invention, illustrated as secured to the surface of the skin 12. As will be appreciated by one of skill in the art, the concentration patch of the present invention may be used for veterinary purposes as well as on humans. In addition, the concentration patch can be used in more diverse applications such as in agriculture or any other environment where a chemical species is to be detected in a fluid and a heat source such as body heat, sunlight, etc. is adaptable to effectuate the distillation or other concentration function of the patch. The preferred use, however, is for determination of preselected chemical species in sweat, and the ensuing discussion is principally directed to that end use.

Moisture expressed from the skin 12 within the perimeter of the test patch 10 first accumulates in a concentration zone 14 beneath the first side of a hydrophobic filter 16. The concentration zone 14 preferably is hydrophilic contains a fluid-permeable medium 20 which may be cotton gauze or other commonly available permeable material. For example, a layer of any of a variety of known fiber webs such as knitted fabrics, or nonwoven rayon or cellulose fibers may be used.

Moisture accumulates in the interfiber spaces of the medium 20 and, under the influence of body heat which is readily conducted from the surface of the skin through the fluid phase, the water component of the perspiration will tend to volatilize.

As previously discussed, the concentration patch 10 is provided with a hydrophobic filter 16. By hydrophobic, I intend to designate any material which will permit the passage of the vapor phase of fluids expressed from the skin, but substantially retain the fluid phase within concentration zone 14. Any of a variety of suitable commercially available microfiltration membrane filters may be used for this purpose, such as the Gore-Tex 0.45 micron Teflon filter manufactured by W. L. Gore & Associates, Inc. (Elkton, Maryland). I use the term hydrophilic in this patent to mean a material which will permit the passage of sweat in the liquid phase.

Adjacent the second side of the hydrophobic filter 16 is a discharge zone 18. As previously discussed, hydrophobic filter 16 retains the fluid phase but permits escape of the vapor phase of the fluid component in perspiration. Thus, the vapor component which primarily consists of vaporized water continuously escapes through the hydrophobic filter 16 exiting the second side thereof into discharge zone 18, which is in communication with the atmosphere. In an alternative embodiment, not separately illustrated, the hydrophobic filter 16 is replaced by a hydrophilic membrane which permits passage of the fluid phase. In this embodiment, fluid, or a combination of vapor and fluid, will be permitted to escape from the concentration patch.

Disposed adjacent the second side of filter 16 in the discharge zone 18 is a flexible permeable outer layer 22. This layer serves to protect the filter 16 against physical damages such as abrasion, and can also serve as a barrier for preventing chemical contamination of the filter material from the outside. Layer 22 may comprise any of a variety of commercially available vapor permeable tapes and films which are known to one of skill in the art. Layer 22 may be distinct from or integral with tape 26 discussed below. Alternatively, depending upon the intended application of the patch, layer 22 may be deleted altogether, where it does not appear that abrasion or external contamination will deleteriously affect the concentration patch 10.

The concentration patch 10 illustrated in FIG. 1 is secured to the surface of the skin by means of a peripheral band of tape 26. Preferably, tape 26 will extend around all sides of patch 10. For example, an annular ring of tape can be die punched for use with a circular patch, or the center of a rectangular piece of tape can be removed to expose layer 22 or filter 16 of a rectangular patch. See FIGS. 1 and 3, respectively. Alternatively, layer 22 and tape 26 could be deleted altogether and layers 16 and 20 could be secured to the surface of the skin by a bandage. One such method would be to capture layers 16 and 20 under a bandage or wrapping surrounding the arm or the leg. In this case, the vapor and/or fluid is permitted to escape through 16 and 20 and into the bandage where it may either collect there or dissipate into the environment.

A large variety of hypoallergenic or other suitable tapes are well known in the art, which may be adapted for use with the concentration patch 10 of the present invention. Different tapes or adhesives may be desirable depending upon the intended use of the test kit, based upon their ability to adhere to the skin during different conditions such as daytime wearing under clothing, during sleep, during profuse sweating for prolonged periods or during showers. It has been determined that the most desirable tapes include multiple perforations which prevent sweat from building up underneath the tape and eventually compromising the integrity of the adhesive. Preferably, a tape, such as Dermiclear marketed by Johnson & Johnson, will be used.

Any of a wide variety of means for securing the concentration patch 10 to the skin 12 may be utilized. For example, the tape 26 can be eliminated and gauze layer 20 provided with a lower adhesive layer to perform the same function. One such adhesive membrane is the MN-100 adhesive membrane manufactured by Memtec of Minnetonka, Minnesota. This membrane is hydrophilic so that it passes fluid as would the gauze layer 20, yet has one adhesive side so that it will stick to the skin. Alternatively, outer protective layer 22 can comprise an annular flange 23, extending radially outwardly beyond the outer edges of filter 16 and gauze 20. See FIG. 2a. The lower surface of the flange 23 is then provided with a suitable adhesive.

The surface temperature of human skin varies regionally, however, it is generally within the range of from about 86° to about 90° F. at rest, and can rise to much higher temperatures under conditions of strenuous exertion. At those temperatures, a number of chemical species of interest for the purpose of the present invention, such as creatine kinase, a high or low density lipoprotein have a sufficiently low vapor pressure that volatilization is not a significant factor in the efficiency of the concentration function. At the same time, the substantial aqueous component will have a sufficiently high vapor pressure that it will tend to volatilize thereby concentrating the less volatile fractions. However, in some applications, the chemical species of interest will have a high enough vapor pressure, even at the resting temperature, such that escape of the vapor phase through the hydrophobic filter 16 of the analyte of interest will disadvantageously impair the efficacy of the test patch. For these analytes, a modified concentration patch must be used.

Referring to FIGS. 2 and 2a, there is disclosed a modified concentration patch 11 according to the present invention for use with an analyte having a propensity to escape through the hydrophobic filter 16 as a vapor under ordinary use conditions. The test patch comprises a concentration zone 14 defined on its inner boundary by the skin 12 to which the concentration patch 11 is secured. The outer boundary of the concentration zone 14 is defined by hydrophobic filter 16, which separates the concentration zone 14 from the discharge zone 18. Disposed in the concentration zone 14, and adjacent the hydrophobic filter 16, is a binder layer 31 for binding and preventing the escape of molecules of the volatile analyte. The binder layer 31 is separated from the gauze layer 20 by a porous layer 28, which may compromise any of a variety of films for retaining the binder layer 331 yet permitting passage of fluid.

In the embodiment illustrated in FIG. 2a, perspiration will pool in the interfiber spaces of the gauze 20, and will percolate through porous layer 28 into the binder layer 31. In that layer, a chemically active or biochemically active binder material will act to selectively bind the volatile analyte, thereby preventing it from escaping as a vapor through hydrophobic filter 16. As discussed in connection with the embodiment illustrated in FIG. 1, it is also possible to replace the hydrophobic filter 16 with a hydrophilic layer, where the presence of fluid on the outside of the test patch would not be undesirable.

The binder layer 31 may comprise any of a variety of binders depending upon the nature of the volatile analyte to be determined. For example, the binder may chemically bind with the analyte or adsorb the analyte to be determined. In addition, the binder layer may comprise a specific binding partner of the analyte to be determined, such as a polyclonal or monoclonal antibody or an antigen matched to a specific antibody desired to be measured in the perspiration.

The concentration patch 11 is additionally provided with tape 26 or another means for securing the patch to the skin of a subject, as has been detailed in connection with the embodiment illustrated in FIG. 1. Concentration patch 11 is illustrated, however, as having a unitary outer layer 22 extending beyond the perimeter of the underlying layers to form an annular flange 23, which is provided with an adhesive on its lower surface. As discussed in connection with the embodiment of FIG. 1, outer protective layer 22 permits the escape of water vapor yet protects the filter material from chemical contamination from the outside.

Referring to FIGS. 3 and 3a, there is disclosed a further embodiment of the test patch of the present invention wherein an inner porous layer 28 and an outer porous layer 30 define a space for containing a microbead layer 32. The inner layer 28 and outer layer 30 preferably comprise the same material, which may be any suitable material for providing an unrestricted flow of fluid through the patch while trapping the microbeads in between. One suitable material for porous layers 28, 30 is the hydrophilic and microporous film known by the name Ultipor (nylon 66) and manufactured by Paul Corporation in Glen Cove, New York. Additional manufacturers of suitable nylon filtration membranes include Micron Separations, Inc. of Westborough, Massachusetts, and Cuno of Meridan, Connecticut. Porous layers 28, 30 may also be comprised of materials other than nylon, such as polycarbonate, modified polyvinylchloride and polysulphone.

The gauze, the inner and outer porous layers and the adhesive tape in all embodiments could be cut to size with conventional dies. The gauze 20 and the inner porous layer 28 could be fixed to the adhesive ring 26 with conventional adhesives, such as used on the adhesive surface itself. Alternatively, they could be heat or ultrasonically bonded together. The proper amount of microbeads could then be placed on top of the inner porous layer and then the outer porous surface attached by similar means. Typically, in a one-inch diameter patch, from about 0.25 grams to about 4 grams of microbeads will be used, and preferably about 0.5 gram will be used. The inner and outer porous surfaces may have to be staked or spot-welded together in some pattern, as will be appreciated by one of skill in the art to prevent the microbeads from collecting in one area.

The free adhesive surface is optimally covered by pull-away paper (not illustrated) with adequate space to be gripped with one's fingers. The patch is packaged in a paper or plastic pouch similar to that used in conventional bandaid packaging. The assembled unit could be terminally sterilized or pasteurized prior to sale. Alternatively, the package could comprise a vapor barrier such as a metallic foil or mylar and even include oxygen or moisture absorbent means such as a small packet of any of a variety of known desiccants, such as silica gel, calcium chloride, calcium carbonate, phosphorous pentoxide or others as will be appreciated by one of skill in the art.

The total thickness of microbead layer 32 can be varied considerably. However, layer 32 is preferably no more than about 3 mm thick since color changes occurring at immobilized sites on thicker layers would not likely be observable in the preferred immunoassay of the present invention. More preferably, the microbead layer is between about 1 mm and about 2 mm thick.

Optimally, the diameter of the beads in microbead layer 32 will be at least about one order of magnitude larger than the diameter of the pores in inner porous layer 28 and outer porous layer 30. For example, the beads contained in microbead layer 32 may have diameters within the range of from about 5 to 50 microns, and preferably within the range of from about 5 to about 10 microns. If 10-micron diameter beads are utilized in the microbead layer 32, for example, inner porous layer 28 and outer porous layer 30 will optimally comprise a median pore size of approximately 1 micron.

Microbead layer 32 may comprise any of a variety of known materials including polystyrene, latex and glass. Beads sized from approximately 0.05 micron to 100 micron which are suitable for the present application are available from Polysciences of Warrington, Pennsylvania.

Microbead layer 32 serves as the support for an immobilized specific binding partner for the analyte to be determined. Thus, a molecule with a high chemical affinity for a specific component in the fluid to be analyzed will be immobilized to the microbeads in microbead layer 32.

Referring to FIG. 5, there is disclosed a further embodiment of the present invention, particularly suited for use under conditions in which profuse sweating is not present, such as in passive insensitive perspiration, wherein the test patch is provided with an impermeable outer layer 42. In order to minimize any back diffusion of fluid into the skin, an absorptive layer 44 is provided to form a reservoir for drawing moisture away from the surface of the skin and through support 46 to which is bound a specific binding partner for at least one analyte to be determined. Layer 44 may include chemical means for binding or collecting moisture such as a desiccant as has been previously discussed, which is suitable for use in proximity to the skin. The patch may be further provided with an underlying porous layer 48 to separate support 46 from the surface of the skin, and the patch is provided with any of the means for attachment to the skin as have been previously discussed.

In one preferred embodiment of the present invention, the analyte to be determined in perspiration is the enzyme creatine kinase MB (CK-MB) which is expressed from the cardiac muscle during myocardial infarction and other cardiac distress. A monoclonal antibody raised against CK-MB can be immobilized to the microbeads in accordance with any of a variety of conventional methods, such as the cyanogen bromide technique described in Pharmacia product literature (Pharmacia, Inc., Piscataway, New Jersey).

The monoclonal antibodies useful in the present invention may be produced and isolated by processes which are well known in the art, such as those discussed by Milstein and Kohler, reported in *Nature*, Vol. 256 at 495-497 (1975). In particular, Jackson describes a method of producing anti-CK-MM (an indicator of the status of skeltal muscles) and anti-CK-MB antibodies in *Clin. Chem.*, 30/7, 1157-1162 (1984).

In accordance with one known process, mice such as Balb/c female mice or other mouse strains or even other suitable animals such as rats or rabbits are immunized with an amount of the CK-MB enzyme to initiate an immune response. The enzyme dosage and immunization schedule for producing useful quantities of suitable splenocytes can be readily determined depending on the animal strain used.

The size and spacing of doses of CK-MB or other antigen are of prime importance in the antibody response. Fortunately, a wide range of antigen does commonly affords immunity against harmful agents. Thus, a small dose of antigen is usually sufficient to initiate an antibody response, i.e., microgram quantities of proteins are frequently adequate. However, a minimum dosage for initiating an immune response does typically exist, although doses of antigen below the minimum dose necessary to initiate an antibody response will usually maintain antibody production which is already in process. For example, an initial immunization with approximately 50$\mu$g of the enzyme may be followed by a hyperimmunization series of five injections.

When certain compounds which are themselves not necessarily antigenic are mixed with an antigen, enhanced antibody production against the antigen occurs, as evidenced by the appearance of large amounts of antibody in the serum, a prolonged period of antibody production, and a response to lower doses of antigen. Such substances are called "adjuvants" and include Freund's incomplete and complete adjuvants and alum gels. Thus, a given dose of antigen is usually more effective when injected subcutaneously with an adjuvant or when injected as repeated small aliquats than when administered intravenously.

Typically, the adjuvants of Freund are preferred. The original "complete" Freund's adjuvant mixture consists of mineral oil, waxes and killed tubercle bacilli. Antigen is added to the adjuvant mixture in an aqueous phase to form a water-in-oil emulsion in which each water droplet is surrounded by a continuous oil phase containing tubercle bacilli. The mixture is commonly injected subcutaneously into experimental animals. Injection stimulates a marked granulomatous reaction with lesions consisting largely of collections of histiocytes, epithelioid cells and lymphocytes. The local lymph node shows a small increase in plasma cells.

Following the immunization with a primary dose of a soluble protein antigen, specific antibodies normally first appear in the serum after a few days increase until about the second week, and thereafter, slowly decline over a period of weeks to months.

The first serum antibodies to appear after antigenization are IgM antibodies. These are usually followed by the appearance of IgG antibodies. Later, as antibody serum levels increase, IgM antibodies disappear, probably as a result of specific feedback suppression of IgG antibodies.

After the "primary response" to a protein has passed, a second dose of the same antigen given months or even years later usually elicits an intense and accelerated "specific secondary response" in which serum antibody usually begins to rise within two or three days of exposure. The serum levels of antibody in a secondary response may reach as high as 10 mg per ml.

The animal is subsequently sacrificed and cells taken from its spleen are suspended in an appropriate medium and fused with myeloma cells, such as those obtainable from the murine cell line Sp2/0-Ag14. The result is hybrid cells, referred to as "hybridomas," which are capable of reproduction in vitro and which produce a mixture of antibody specific to each of the various recognizable sites on the CK-MB enzyme.

The myeloma cell line selected should be compatible with the spleen cells, and optimally of the same species. Although the murine cell line Sp2/0-Ag14 has been found to be effective for use with mouse spleen cells, other myeloma cell lines could alternatively be used. See, for example, *Nature*, Vol. 276 at pp. 269-270 (1978).

The myeloma cell line used should preferably be of the so-called "drug resistant" type, so that any unfused myeloma cells will not survive in a selective medium, while hybrid cells will survive. A variety of drug resistant myelomas are known.

The mixture of unfused spleen cells, unfused myeloma cells and fused cells are diluted and cultured in a selective medium which will not support the growth of the unfused myeloma cells for a time sufficient to allow death of all unfused cells. A drug resistant unfused myeloma cell line will not survive more than a few days in a selective medium such as HAT (hypoxanthine, aminopterin and thymidine). Hence, the unfused myeloma cells perish. Since the unfused spleen cells are nonmalignant, they have only a finite number of generations until they fail to reproduce. The fused cells, on the other hand, continue to reproduce because they possess the malignant quality contributed by the myeloma parent and the enzyme necessary to survive in the selected medium contributed by the spleen cell parent.

The supernatant from each of a plurality of hybridoma containing wells is evaluated for the presence of antibody to a specific site unique to the CK-MB enzyme structure. Hybridomas are then selected producing the desired antibody to that specific site. This selection may be, for example, by limiting dilution, in which the volume of diluent is statistically calculated to isolate a certain number of cells (e.g., 1 to 4) in each separate well of a microtiter plate. In this way, individual hybridomas may be isolated for further cloning.

Once the desired hybridoma has been selected, it can be injected into host animals of the same species as those used to prepare the hybridoma, preferably syngenic or semisyngenic animals. Injection of the hybridoma will result in the formation of antibody producing tumors in the host after a suitable incubation time, resulting in a very high concentration of the desired antibody in the blood stream and in the peritoneal exudate of the host. Although the hosts have normal antibodies in their blood and exudate, the concentration of these normal antibodies is only about 5% of the concentration of the desired monoclonal antibody. The monoclonal antibody may then be isolated in accordance with techniques known in the art.

Alternatively to raising anti-CK-MM monoclonals as described, the components of a commercially available diagnostic kit could be utilized, which incorporates the CK-MM enzyme chemically bound to a bead support. A suitable kit marketed as the Isomune-Ck Diagnostic Kit by Roche of Nutley, New Jersey, is one commercially available candidate. This kit includes a goat antisera to human CK-MM and donkey antigoat antibody covalently bound to styrene beads. A mixture would produce an immobilized conjugate having a specific affinity for human CK-MM. A more direct and less expensive procedure, however, would be to immobilize the anti-CK-MM monoclonal antibody directly to the microbead support in accordance with methods now well known in the art.

The antibody which is to be used for the purpose of complexing with CK-MB may be immobilized on any of a variety of supports known in the art. For example, anti-CK-MB antibody may be bound to polysaccharide polymers using the process described in U.S. Pat. No. 3,645,852. Alternatively, the antibody may be bound to supports comprising filter paper, or plastic beads made from polyethylene, polystyrene, polypropylene or other suitable material as desired. Optimally, the support will take the form of a multiplicity of microbeads which can conveniently be formed into microbead layer 32, illustrated in FIG. 3a.

As an alternative to a microbead support layer, the specific binding partner could be immobilized directly to the inner porous layer 20 or 28 on FIG. 3a or to the underside of filter 16 of FIG. 1a. In this manner, the need for microbead layer 32 could be eliminated entirely. Hydrophilic membranes which are specifically designed for binding antibody proteins are commercially available, such as Zetapor from Cuno, and Protrans, available from ICN in Costa Mesa, California.

Referring to FIG. 4, there is disclosed a reagent packet for use with the concentration kit of the present invention. The reagent packet 34 comprises a container 36 having a removably secured top 38. A flap 40 on the top 38 facilitates gripping the top 38 and peeling away from container 36 to reveal the reagent contained therein.

A variety of well known immunoassay sohemes for visualizing the presence of a predetermined analyte are well known in the art, and need not be detailed here. However, the optimal immunoassay scheme is one which is simple and requires the fewest steps. For example, in a concentration patch of the present invention designed for determining both the presence of CK-MM and CK-MB enzyme, the immobilized specific binding partner for each of those enzymes will be segregated to separate regions of the test patch. In this manner, if an enzyme-linked immunoassay system is utilized, a common enzyme and a common substrate could be used. Optimally, however, a different color would be used to express the presence of different analytes.

Alternatively, a stain such as used in protein electrophoresis, for example, Coomassie brilliant blue or amido black 10b, can be bound to purified analyte contained in the reagent packet 34. When a test patch is immersed in the packet 34, any antibodies on the microbeads that are unbound by analyte in the perspiration will become occupied by stained purified analyte in the packet 34. There will thus be an inverse relationship between the amount of stain absorbed by the patch and the amount of enzyme passed through the patch. In this embodiment, the user would place the patch in the fluid of the packet 34, wait for some period of time such as 30 seconds or more, rinse the patch under tap water and relate the resultant color of the patch to the presence of the enzyme. A color comparison chart may be provided to aid in this interpretation.

Alternatively, the user could support the test patch on an open vessel, such as a small jar or vial, or empty container similar in design to reagent packet 34 securing the adhesive border of the patch to the rim of the vessel, and then pour contents of packet 34 on top of the test patch. Gravity would assist the transport of the contents of packet 34 through the test patch to maximize the efficiency of the stain/binding reaction, and to facilitate visualization of the color change.

The system could readily be designed so that the user performs his interpretation of the concentration of the unknown not in the patch at all but by observing the packet contents once said contents have traversed the patch. This method would be similar to conventional ELISA assay methods where the packet contents contain enzyme conjugates which will react to specific enzyme substrates. The enzyme substrates would be added to the packet contents after those contents transversed the test patch.

If the perspiration contained molecules of interest, they would bind to the specific immobilized binding partner on the patch. If this occurred, enzyme conjugates in the packet would pass freely across the test patch and enzymatically modify the enzyme substrate producing a controlled color change in the solution in the packet. If the perspiration reached the desired molecules of interest, enzyme conjugates would then be bound in transit across the patch and would be unavailable to cause color change in the substrate solution. Other immunoassay schemes can be readily adapted for use in the present invention by one of skill in the art.

Although the concentration patch of the present invention could be used for any of a variety of body fluids, perspiration is the desired fluid due to its dependable supply and its similarity to blood, albeit with lower analyte concentrations. Saliva also appears to contain many of the chemical components of blood, however, often at even lesser concentrations than found in sweat.

In performing the method of the present invention, the concentration patch may advantageously be located on different regions of the body depending upon a variety of factors. It is well known that the quantity of perspiration generated is a function of both the location on the body, as well as the physical activity during and immediately preceding collection. This is due to both different densities of sweat glands on different regions of the body, as well as to certain regulatory functions of those glands.

Sweat glands are classified to be either of two types. Eccrine type function primarily to regulate body temperature through their relationship to evaporative heat loss. It is the eccrine type sweat gland that provides the sweat associated with exercise and is therefore the source of perspiration of interest for many applications of the concentration patch of the present invention. Apocrine type sweat glands are larger secreting elements which are localized only in relatively isolated areas of the body such as the axilla, pubic and mammary areas.

Although the etiology of perspiration is relatively complex, it is known to be caused by both mental states such as mental exercise and emotional stress; thermal stress, as the sedentary body's response to temperature control; and exercise stress a the physically active body's response to temperature control.

In addition to the foregoing distinctions, perspiration can be either insensible or sensible. Insensible sweat appears to be caused by water diffusion through dermal and epidermal layers. Its purpose appears to be not related to thermal regulation at all, but to aid in such things as the improvement of mechanical interaction between the skin and surfaces to facilitate grip. Further complexities arise with regard to the spatial distribution of sweat glands and the flow rates of the various types of perspiration. Specialized areas of the palms and soles of the feet sweat continuously, although at a very low rate. The rate of insensible perspiration is dependent upon the position of the particular area in question relative to the heart. For example, elevating a limb over the heart decreases the insensible perspiration rate.

At temperatures of less than about 31° C. in a resting human adult, insensible perspiration proceeds at a rate of between about 6-10 grams per square meter per hour from the skin of the arm, leg and trunk, up to about 100 grams per square meter per hour for palmer, planter and facial skin. The latter three areas jointly account for approximately 42% of the total water loss from the body under non-sweating conditions, which generally means an air temperature of between about 24-26° C. Such insensible perspiration first begins on the dorsal surfaces of the foot and spreads to higher places on the body as the temperature increases. One reported study determined that the average water loss due to insensible perspiration for a body surface area of 1.75 square meters ranged from 381 ml, 526 ml and 695 ml per day at ambient temperatures of 22° C., 27° C. and 30° C., respectively.

In contrast to insensible perspiration which does not appear to be associated with a particular surface element of the skin, sensible perspiration has been associated with the eccrine gland. The number of actively secreting eccrine glands varies among individuals and depends upon the part of the body observed and the type of sweat response created. Maximum gland density varies from between about 200 per square centimeter on the forearm to over 400 per square centimeter on the thenar eminence.

The appearance of sensible sweat begins at either when the skin temperature exceeds about 94° F. or the rectal temperature exceeds about 0.2° F. over normal core temperature. Maximum rates of sweat volume loss can be as high as 2 liters per hour in average subjects and can be as high as 4 liters per hour for brief periods. Sensible perspiration begins in the distal parts of the lower extremities and progresses upward as the environmental temperature is elevated. Thus, the dorsum of the foot begins to sweat long before the chest. The pattern of sensible sweat response also shifts from one region of the body to another as the thermal stress increases. Under mild thermal stress, sweating is present mainly in the lower extremities. As the thermal stress further increases, sweating spreads to the trunk. Due to its large surface area, the trunk becomes the dominant water loss surface. Eventually, extremely high rates are found in the trunk while rates in the lower extremities may actually decline. The forehead can produce extremely high sweat rates but is among the last areas to sweat in response to thermal stress.

As has been described previously, a large variety of chemical species which are detectable in blood are also present in sweat, although typically in a much lesser concentration. Early investigation into the composition centered on electrolytes, including sodium, chloride, calcium and potassium. Extreme individual variation was found among individuals, and the electrolyte composition also differed depending upon whether the sweat was stimulated by thermal, mental or other etiology.

Further research has identified numerous additional components in sweat, including both electrolytes and more complex biological molecules. Some illustrative chemical species which have been identified in sweat are identified in Table I below.

TABLE I

Chemical Components of Sweat

| | |
|---|---|
| diphtheria antitoxin | sulfates |
| ascorbic acid | iodine |
| thiamine | iron |
| riboflavin | fluorine |
| nicotinic acid | bromine |
| amino acids | bismuth |
| ethanol | lactic acid |
| antipyrine | pyruvate glucose |
| creatinine | nitrogen |
| C-14 methylurea | ammonia |
| C-14 acetamide | uric acid |
| C-14 urea | nicotine |
| thiourea | morphine |
| paraaminohippuric acid | sulfanilamide |
| mannitol sucrose | atabrin |
| lactate | methadone |
| sodium chloride | phencyclidine |
| potassium | aminopyrine |
| calcium | sulfaguanidine |
| magnesium | sulfadiacine |
| phosphorous | amphetamines |
| manganese | |

Since most of the components listed in Table I are non-volatile, they will be trapped in the concentration zone 14 of the concentration patch 10 illustrated in FIG. 1. However, some components, most notably ethanol, would volatilize under the influence of body heat thereby enabling escape in the vapor phase through the hydrophobic filter 16. Where the analyte to be determined is ethanol or another volatile component, the concentration patch of the present invention may be modified as described in connection with the embodiment illustrated in FIG. 2.

One specific application of the present invention is the dual determination of skeletal muscle and cardiac muscle status as a result of exercise. This application is illustrated in the following Examples, which describe only a single application of the present invention.

EXAMPLE 1

A dermal concentration patch is constructed in accordance with the embodiment illustrated at FIG. 3. The gauze layer is prepared by cutting a circular patch having an approximately 1-inch diameter from a Johnson & Johnson non-stick gauze pad. The inner and outer porous layers are next prepared by cutting two circular patches of Ultipor (nylon 66), from Pall Corporation in Glen Cove, New York. Ultipor membrane is both hydrophilic and microporous, and a membrane is selected having, for example, a 1 micron rating. The microbead layer is prepared by covalently bonding monoclonal antibody raised against CK-MB to a multiplicity of polystyrene beads having a mean particle size of at least about 10 microns.

The concentration patch is assembled by distributing approximately 1 gram of microbeads across the surface of one of the porous layers. The second porous layer is thereafter disposed adjacent the microbeads, and the gauze layer is next placed on top of the second porous layer. At this point, the patch is upside-down. The peripheral edges of each of the first and second porous layers and the gauze layers are secured together by conventional heat-sealing techniques. Thereafter, the subassembly is turned over and an annular torus of adhesive tape having approximately a 2-inch outside diameter and slightly less than a 1-inch inside diameter is secured thereto to produce a finished concentration patch.

EXAMPLE 2

The concentration patch of Example 1 is then secured to the chest of a healthy 40-year old male and worn throughout a 36-mile (130-minute) bicycle ride. Upon removal of the concentration patch following the ride, the test patch is immersed in a first solution containing an excess of enzyme labeled anti-CK-MB for approximately 30 minutes, to permit conjugation of labeled antibody with immobilized analyte. The patch is then rinsed under tap water to remove unbound labeled antibody and immersed in a second solution containing a substrate for the bound enzyme label, which undergoes a color change when acted upon by the enzyme. Appearance of color through the top porous layer indicates the presence of CK-MB, and possible cardiac injury. Comparison to a color chart permits rough quantification.

Although this invention has been described in terms of certain preferred embodiments, other embodiments that are apparent to those of ordinary skill in the art are also within the scope of this invention. Accordingly, the scope of the invention is intended to be defined only by reference to the appended claims.

We claim:

1. A dermal concentration patch for determining the presence of an analyte inn a subject mammal's perspiration, comprising:
    a water permeable support layer having a first and a second side;
    at least one reagent immobilized to the support layer;
    means for removably securing the first side of the support layer in fluid communication with the subject's skin,
    said concentration patch having sufficient permeability so as to permit water to escape through the support layer and outside of the concentration patch, wherein the reagent comprises a specific binding partner for the analyte to be determined.

2. A dermal concentration patch as in claim 1, wherein the support layer is hydrophobic.

3. A dermal concentration patch as in claim 1, further comprising an adhesive on the first side of the support layer and a hydrophilic permeable membrane on the second side of the support layer.

4. A dermal concentration patch as in claim 1, wherein the means for securing comprises adhesive tape.

5. A dermal concentration patch as in claim 1, wherein the reagent comprises an antibody having an affinity for the analyte to be determined.

6. A dermal concentration patch as in claim 1, wherein the reagent comprises antibody for at least one of creatine kinase MB and creatine kinase MM.

7. A concentration patch for concentrating components of a body fluid under the influence of body heat, comprising:
    a concentration zone adapted for communication with a source of body fluid;
    a discharge zone exposed too the atmosphere;

a hydrophobic membrane, separating the concentration zone from the discharge zone; and means on the patch for removably securing the concentration zone in communication with the source of body fluid, wherein volatile components of the body fluid accumulated in the concentration zone are driven through the hydrophobic membrane in the vapor phase, but not in the liquid phase, thereby concentrating non-volatile desired components in the concentration zone.

8. A concentration patch as in claim 7, wherein the means for removably securing the concentration zone comprises an adhesive surface, the source of body fluid comprises skin, and the concentration zone has a first side adapted to be placed in fluid communication with said skin, and further comprising:

an inner porous layer on the first side of the concentration zone for spacing the concentration zone apart from the skin.

9. A concentration patch as in claim 8, further comprising an outer protective porous layer in the discharge zone.

10. A dermal concentration patch for concentrating components of perspiration expressed through the skin under the influence of body heat, comprising:

a concentration zone adapted to be disposed in fluid communication with the skin, said zone being formed of a material which accumulates said perspiration; and a hydrophobic membrane adjacent the concentration zone, said membrane adapted to retain volatile and non-volatile components of said perspiration in the fluid phase within the concentration zone but permitting passage of volatile components of said perspiration in the vapor phase, wherein said concentration patch has sufficient permeability so as to permit water to escape through said concentration zone and hydrophobic membrane and outside of the concentration patch.

11. The concentration patch of claim 10, additionally comprising means on the patch for removably securing the concentration zone in communication with the skin.

12. A dermal concentration patch for concentrating components of a body fluid under the influence of body heat, consisting essentially of:

a hydrophilic concentration zone adapted for communication with a source of said body fluid;

a hydrophobic membrane adjacent said concentration zone, said membrane adapted to concentrate non-volatile components of said body fluid in said concentration zone by permitting passage of volatile components therethrough in the vapor phase whilst retaining non-volatile and volatile components in the concentration zone in the fluid phase; and means on the patch for removably securing the concentration zone in communication with the source of body fluid.

13. A concentration patch according to either claim 7 or 10, wherein said concentration zone comprises a hydrophilic material.

14. A concentration patch according too any one of claim 7, 10 or 12, wherein said concentration zone comprises a material selected from the group consisting of: knitting fabrics, nonwoven rayon, cellulose fibers and cotton gauze.

15. A concentration patch according to any one of claims 7, 10 or 12, wherein said hydrophobic membrane comprises teflon filter material.

16. A concentration patch according to either claim 7 or 10, wherein said hydrophobic membrane has a first side and a second side, said first said being adjacent said concentration zone, additionally comprising a flexible permeable outer layer adjacent said second side.

17. A concentration patch according too any one of claims 7, 11 or 12, wherein said means for removably securing the concentration zone comprises adhesive tape or a lower adhesive layer on said concentration zone.

18. A method for determining the presence of an analyte in a body fluid, comprising the steps of:

accumulating a quantity of a body fluid from a subject mammal in a concentration patch;

removing from the concentration patch a substantial portion of the water component from the fluid under the influence of body heat too form a concentrate; and binding at least one analyte in the concentrate to an immobilized specific binding pattern of that analyte.

19. A method as in claim 18, further comprising the step of expressing ann indicium of the concentration of the analyte.

20. A method as in claim 18, wherein the accumulating step is conducted in a porous layer.

21. A dermal concentration patch for the noninvasive determination of at least one preselected low-concentration analyte in a body fluid expressed through the skin as perspiration without the need for conventional instrumentation, comprising:

a first layer adapted to be disposed in fluid communication with the skin, said layer being formed of a material which accumulates the body perspiration which vaporizes under the influence of body heat which is readily conducted from the surface of the skin through the accumulated perspiration fluids;

a second layer adjacent the first layer, the second layer being formed of a material which will permit the passage of the vapor phase of fluids expressed from the skin but retain the fluid phase thereof within said first layer; and an immobilized reagent in contact with the first layer and with the accumulated perspiration for selectively binding with at least one preselected analyte, said concentration patch having sufficient permeability so as to permit water to escape through said first and second layers and outside of the concentration patch.

22. A dermal concentration patch for the noninvasive determination of at least one preselected low-concentration analyte in a body fluid expressed through the skin as perspiration without the need for conventional instrumentation, comprising:

a first layer adapted to be disposed in fluid communication with the skin, said layer being formed of a material which accumulates the body perspiration which is lost under the influence of body heat;

a second layer adjacent the first layer, the second layer formed of a material which will permit passage of the liquid expressed from the skin; and an immobilized reagent in the second layer which selectively binds at least one preselected analyte, said concentration patch having sufficient permeability so as to permit water to escape through said first and second layers and outside of the concentration patch.

23. A dermal concentration patch for determining the presence of an analyte in a subject mammal's perspiration, consisting essentially of:
- a water permeable support layer having a first and a second side;
- at least one specific binding partner for the analyte to be determined immobilized to the support layer; and
- means for removably securing the first side of the support layer in fluid communication with the subject's skin without preventing water from escaping through the support layer and outside of the concentration patch.

24. A method for determining the presence of an analyte in a body fluid from a subject mammal, comprising the steps of:
- removably securing a concentration zone in fluid communication with a source of said body fluid;
- accumulating a quantity of said body fluid from said subject mammal in said concentration zone; and
- concentrating non-volatile components of said body fluid in said concentration zone by permitting passage of volatile components through a hydrophobic membrane in the vapor phase whilst retaining non-volatile and volatile components in the concentration zone in the fluid phase underneath said hydrophobic membrane.

25. The method of claim 24, additionally comprising analyzing the concentrated components of said body fluid in said concentration zone for the presence of said analyte.

26. The method of claim 25, wherein said analyte is selected from the group consisting of: diphtheria antitoxin, ascorbic acid, thiamine, riboflavin, nicotinic acid, amino acids, antipyrine, creatine, methylurea, acetamide, urea, thiourea, paraaminohippuric acid, mannitol, sucrose, lactate, sodium chloride, potassium, calcium, magnesium, phosphorus, manganese, sulfates, iodine, iron, fluirine, bromine, bismuth, lactic acid, pyruvate glucose, nitrogen, ammonia, uric acid, nicotine, morphine, sulfanilamide, atabrin, methadone, phencyclidine, aminopyrine, sulfaguanidine, sulfadiacine, amphetamines, creatine kinase, and high and low density lipoproteins.

27. The method of claim 24, wherein the securing step comprises application f adhesive tape.

28. The method of claim 24, wherein the securing step comprises securing the concentration zone in fluid communication with the skin of said mammal.

29. The method of claim 28, wherein the body fluid comprises perspiration.

30. The method of claim 24, wherein the concentrating step comprises hating said body fluid under the influence of body heat from said mammal.

* * * * *

UNITED STATES PATENT AND TRADEMARK OFFICE
CERTIFICATE OF CORRECTION

PATENT NO. : 5,076,273  
DATED : December 31, 1991  
INVENTOR(S) : Donald W. Schoendorfer, et al.

Page 1 of 2

It is certified that error appears in the above-identified patent and that said Letters Patent is hereby corrected as shown below:

In column 1, line 7, "abandoned, is" should read --abandoned, which is--.

In column 4, lines 1-2, "hydrophilic contains" should read --hydrophilic and contains--.

In column 10, line 39, "sohemes" should read --schemes--.

In column 11, line 64, "stress a the physically" should read --stress as the physically--.

In column 14, line 35 (the second line of Claim 1), "an analyte inn" should read --an analyte in--.

In column 14, line 68 (the sixth line of Claim 7, "exposed too" should read --exposed to--.

In column 15, line 65 (the second line of Claim 14), "claim 7, 10 or 12" should read --claims 7, 10 or 12--.

In column 16, line 23 (the tenth line of Claim 18), "binding pattern" should read --binding partner--.

In column 16, line 26 (the second line of Claim 19), "ann indicium" should read --an indicium--.

In column 18, line 12 (the eighth line of Claim 26), "fluirine" should read --fluorine--.

UNITED STATES PATENT AND TRADEMARK OFFICE
CERTIFICATE OF CORRECTION

PATENT NO. : 5,076,273
DATED : December 31, 1991
INVENTOR(S) : Donald W. Schoendorfer, et al.

It is certified that error appears in the above-identified patent and that said Letters Patent is hereby corrected as shown below:

In column 18, line 19 (the second line of Claim 27), "application f adhesive" should read --application of adhesive--.

In column 18, line 26 (the second line of Claim 30), "hating said body fluid" should read --heating said body fluid--.

Signed and Sealed this

Twenty-ninth Day of August, 1995

Attest:

BRUCE LEHMAN

*Attesting Officer*    *Commissioner of Patents and Trademarks*